United States Patent [19]

Matthews

[11] Patent Number: 5,244,811
[45] Date of Patent: Sep. 14, 1993

[54] METHOD AND SYSTEM FOR DETERMINING ORGANIC MATTER IN AN AQUEOUS SOLUTION

[75] Inventor: Ralph W. Matthews, Georges Hall, Australia

[73] Assignee: Commonwealth Scientific and Industrial Research Organization, Campbell, Australia

[21] Appl. No.: 787,732

[22] Filed: Nov. 4, 1991

Related U.S. Application Data

[63] Continuation of Ser. No. 425,193, Oct. 13, 1989, abandoned.

[30] Foreign Application Priority Data

Mar. 2, 1987 [AU] Australia .................. PI0601

[51] Int. Cl.$^5$ .................. G01N 21/75; G01N 33/18
[52] U.S. Cl. .................. 436/146; 436/145; 436/150; 436/159; 436/905; 422/80; 422/82.02
[58] Field of Search .................. 436/145–146, 436/127, 150, 159, 177, 905; 422/82.02, 78–80

[56] References Cited

U.S. PATENT DOCUMENTS

| | | | |
|---|---|---|---|
| 4,273,558 | 6/1981 | Mar . | |
| 4,619,902 | 10/1986 | Bernard | 422/80 X |
| 4,775,634 | 10/1988 | Sienkiewicz | 422/80 X |
| 4,861,484 | 8/1989 | Lichtin et al. | 210/764 X |
| 4,863,608 | 9/1989 | Kawai et al. | 210/748 X |
| 4,868,127 | 9/1989 | Blades et al. | 436/146 |
| 4,892,712 | 1/1990 | Robertson et al. | 210/763 X |

FOREIGN PATENT DOCUMENTS

| | | |
|---|---|---|
| 76028 | 1/1988 | Australia . |
| 51-138496 | 5/1975 | Japan . |
| 55-23418 | 2/1980 | Japan . |
| 60-118236 | 6/1985 | Japan . |
| 1185290 | 3/1970 | United Kingdom . |

OTHER PUBLICATIONS

Grant & Hackh's Chemical Dictionary, 5th ed., McGraw-Hill Book Company, New York, p. 609 (1987).
Pruden, A. L. et al., Environmental Science and Technology, vol. 17, No. 10, 1983, 628–631.
Matthews, R. W., "Photocatalytic Oxidation of Chlorobenzene in Aqueous Suspensions of Titanium Dioxide" J. Catalysis, 97, 1986, 565–568.
Derwent Abstract Accession No. 84-303465/49, Apr. 1983.
Haverty, J. L. Ultrapure Water Sep./Oct. 1984, (pp. 29–31).
Neta, P. et al. J. Phys. Chem. 1986, 90(19): 4644–4648.
Matthews, R. W. J. Phys. Chem. 76(9): 1265–1272 (1972).

Primary Examiner—James C. Housel
Assistant Examiner—Jeffrey R. Snay
Attorney, Agent, or Firm—Ladas & Parry

[57] ABSTRACT

A method and system for determining organic matter in an aqueous solution including an oxidizing agent are disclosed. The method includes contacting the solution with a semiconductor which is capable of photocatalytically oxidizing the organic matter, illuminating the semiconductor with light of a wavelength or having a spectrum whereby the semiconductor photocatalytically oxidizes the organic matter in the solution to form a photocatalytic by-product(s), and detecting the by-product(s). The system includes a photocatalytic reactor (104) having a semiconductor, which is capable of photocatalytically-oxidizing the organic matter to form a photocatalytic by-product(s), disposed therein so as to contact the solution when disposed in the reactor, an illumination source (103) disposed to illuminate the semiconductor in the reactor wherein the source is capable of emitting light of a wavelength or having a spectrum whereby upon illumination of the semiconductor in contact with the solution the semiconductor photocatalytically-oxidizes the organic matter in the solution, and a device for detecting the by-product(s) (108, 109) operatively associated with or operatively coupled to the reactor.

23 Claims, 6 Drawing Sheets

METHOD AND SYSTEM FOR DETERMINING ORGANIC MATTER IN AN AQUEOUS SOLUTION

This is a continuation of copending application Ser. No. 07/425,193 filed on Oct. 13, 1989, now abandoned, which was a national stage application of International Application PCT/AU88/00059 filed on Mar. 2, 1988 and which designated the U.S.

TECHNICAL FIELD

This invention relates to methods systems for qualitatively and quantitatively determining organic matter in an aqueous solution including an oxidizing agent.

BACKGROUND ART

Two techniques in common usage for determining total organic carbon (TOC) in aqueous solutions are the combustion method and the photooxidation method. In both, organic matter is oxidized to carbon dioxide which is subsequently measured by standard techniques such as infrared, conductivity, gas chromatography or flame ionization detection after reduction to methane. The combustion method is capable of rapid analysis on small samples (100 $\mu$L to 200 $\mu$L), however, it is not ideally suited for the accurate measurement of low TOC concentrations (less than 1 ppm). The photooxidation method is better suited to the determination of lower TOC concentrations than the combustion method since much larger samples can be used (up to 100 mL).

In the photooxidation method ultraviolet light of 180 to 260 nm wavelength or shorter is commonly used. Low pressure mercury vapour lamps have a major emission at 184.9 and medium pressure mercury lamps have a major emission at 253.7 nm. Both types of lamp may be used to effect photochemical oxidations (Danny M. Mar U.S. Pat. No. 4,273,558). Persulfate ions are frequently added to promote the oxidation (Janice L. Haverty, Ultrapure Water, Sep./Oct. 1984). Regardless of which ultraviolet lamp is used it is essential to use a quartz envelope around the lamp and between the lamp and the solution in order to transmit a maximum amount of ultraviolet light.

The photo-induced oxidation is believed to involve hydroxyl radicals in the case of the 184.9 nm light and sulfate radicals when persulfate photooxidation is used. Sulfate radicals are generally less effective than hydroxyl radicals in the oxidation of organics (P. Neta and R. E. Huie, J. Phys. Chem. 90, 4644 [1986]) but react with water to give hydroxy radicals (R. W. Matthews, H. A. Mahlman, and T. J. Sworski, J. Phys. Chem. 76, 1265 [1972]). Whether the photooxidation proceeds via hydroxyl radicals or sulfate radicals, the rate is enhanced by the addition of persulfate presumably because of the greater yield of photolytically generated oxidizing radicals. In any event one of the main disadvantages of the photooxidation method is that different organic compounds very often have different rates of photooxidation unless the relative ratios and the nature of organic compounds within a given aqueous solution are known, it is difficult to accurately compare the yield of carbon dioxide liberated therefrom as a result of photooxidation, with a calibration curve of the yield of carbon dioxide liberated from an aqueous solution of known organic compounds of different relative ratios and/or which are different from the aforementioned organic compounds.

A need exists for a quick, simple and economical method of detecting the presence of an organic compound in water or an aqueous composition for a variety of applications. For example formalin solutions are used to disinfect kidney dialysis machines after change of filters. After rinsing with water it must be ensured that no trace of formaldehyde remains in the machine and thus it is necessary to analyse the water used for the final rinse.

The present inventor has found that photocatalytic oxidation over thin films of titanium dioxide illuminated with near ultraviolet light is a powerful method of oxidizing dissolved organic solutes in aqueous solution. The ambient oxygen dissolved in the aqueous solution is the oxidizing agent and the photogenerated holes or hydroxyl radicals are the photocatalytic reactive intermediates. The reaction appears to be quite general for all organics in solution. A number of organic compounds have been shown to be totally mineralized (that is, converted to inorganic products) and it seems likely that this will occur with most organic compounds. Since photocatalytic oxidation is a fast, simple and inexpensive technique it would be advantageous if the technique could be utilized to detect the presence of an organic compound in water or an aqueous composition.

It is an object of this invention to provide a method and system for qualitatively and quantitatively determining organic matter in an aqueous solution including an oxidizing agent.

DISCLOSURE OF INVENTION

Unexpectedly the inventor has found that the amount of carbon dioxide liberated by photocatalytically oxidising a wide variety of organic compounds in an aqueous solution is relatively insensitive (rate of formation of $CO_2$ from a wide variety of organic compounds within a factor of 4.6—see Table 1 in Australian Provisional Patent Specification No PH7074) to the nature of the organic compound. The present inventor has found the absence or presence of photocatalytically oxidized by-products of an organic compound in water or an aqueous composition can be utilised to indicate whether the organic compound was originally present in the liquid. The inventor has also found that when the organic compound is present in the water or in the aqueous composition that after photocatalytic oxidation of the organic compound the concentration of resultant oxidized by-products can be utilized to determine the initial concentration of the organic compound in the liquid.

According to a first embodiment of this invention there is provided a method for qualitatively determining organic matter in an aqueous solution including an oxidizing agent which method comprises:

(a) contacting the solution with a semiconductor which is capable of photocatalytically oxidising the organic matter;

(b) illuminating the semiconductor with light of a wavelength or having a spectrum whereby the semiconductor photocatalytically oxidizes the organic matter in the solution to form a photocatalytic by-product(s); and (c) detecting the by-product(s).

According to a second embodiment of this invention there is provided a method for quantitatively determining organic matter in an aqueous solution comprising the method as defined in the first embodiment and further comprising:

(d) measuring a parameter of the by-product(s) related to the concentration or amount thereof;

(e) determining the concentration of the organic matter in the solution from the parameter of the by-product(s).

In one preferred method the aqueous solution is an acidified aqueous solution whereby the by-product comprises carbon dioxide.

In another preferred method the aqueous solution is acidified after step (b) to convert the by-products comprising inorganic carbonate(s) to carbon dioxide. The carbon dioxide can be purged from the aqueous solution with a gas other than carbon dioxide and the purged carbon dioxide can be detected. The amount of the purged carbon dioxide is then determined and the total carbon concentration in the solution is determined from the amount of the purged carbon dioxide.

Preferably the amount of the purged carbon dioxide is determined by dissolving the purged carbon dioxide in water and measuring the change in conductivity of the water caused by the dissolving.

Typically the by-product(s) is detected by measuring the change in an electrical characteristic of the solution caused by the photocatalytic oxidation, the amount of the by-product is determined from the magnitude of the change and the concentration of the organic matter is determined from the amount. It is preferred that the electrical characteristic is conductivity.

Generally the solution is agitated during the illuminating. The solution can be agitated by bubbling and/or pumping air or oxygen through the solution.

According to a third embodiment of this invention there is provided a system for qualitatively determining organic matter in an aqueous solution including an oxidizing agent which system comprises:

(i) a photocatalytic reactor having a semiconductor, which is capable of photocatalytically-oxidizing the organic matter to form a photocatalytic by-product(s), disposed therein so as to contact the solution when disposed in the reactor;

(ii) an illumination source disposed to illuminate the semiconductor in the reactor wherein the source is capable of emitting light of a wavelength or having a spectrum whereby upon illumination of the semiconductor in contact with the solution the semiconductor photocatalytically-oxidizes the organic matter in the solution; and (iii) means for detecting the by-product(s) operatively associated with or operatively coupled to the reactor.

According to a fourth embodiment of this invention there is provided a system for quantitatively determining organic matter in an aqueous solution comprising the system as defined in the third embodiment and further comprising:

(iv) means for measuring a parameter of the by-product(s) related to the concentration or amount thereof, operatively associated with or operatively coupled to the means for detecting the by-product(s).

Preferably the system of the fourth embodiment further includes:

(v) calculating means operatively associated with or operatively coupled to the means for measuring a parameter, for calculating the concentration of the organic matter in the solution from the parameter of the by-product(s).

The oxidizing agent can be ambient oxygen or hydrogen peroxide or other suitable agent.

Typically the systems of the third and fourth embodiments also include means for purging the carbon dioxide from the aqueous solution with a gas other than carbon dioxide, the means for detecting is adapted to detect the purged carbon dioxide and the means for purging is operatively associated with or operatively coupled to the reactor. Preferably the means for detecting is a conductively cell is operatively associated with or operatively coupled to the reactor.

Generally the systems of the third and fourth embodiments further includes means for agitating the solution, operatively associated with or operatively coupled to the reactor such as a pump.

In principle, any semiconductor which can photocatalytically oxidise organic carbon compounds to carbon dioxide can be used. Titanium dioxide is especially preferred. Other preferred photocatalytic metal oxides include niobium pentoxide, strontium titanate, indium trioxide, calcium titanate, tungsten trioxide, barium titanate, iron (III) oxide, zinc oxide, potassium tantalate, tin dioxide and cadmium oxide. Other photocatalytic metal oxides include hafmium oxide, zirconium oxide, tantalum pentoxide, chromium trioxide and yttrium trioxide. It is especially preferred that the semiconductor is relatively stable in aqueous solution.

The metal oxide particles can be loaded with a metal catalyst or metal oxide catalyst such as Pt, Ag, Au, Ru, $RuO_2$, Pd and PdO or mixtures thereof.

The semiconductor is preferably in the form of fine particles preferably less than 500 microns, more preferably less than 50 microns and even more preferably less than 5 microns. It is especially preferred that the average particle size of the metal oxide particles is about 30 nm. In another preferred form the semiconductor is coated on a substrate which is preferably selected from the group consisting of silica, teflon, silica gel, soda glass, diatomaceous earth, borosilicate glass, aluminium oxide, mullite, cordierite, sintered porous glass and glass mesh. It is especially preferred that when semiconductor photocatalytic metal oxides are coated onto any of the above substrates that the process of coating is one of the coating processes disclosed in Australian Provisional Specification No. PH7074. A preferred form of substrate is bead form of diameters in the range between 0.01 mm to 5 mm. It is preferred that the substrate is in the form of particles of uniform size such as uniformly-sized beads. With respect to titanium dioxide these substrates have the following advantages:

(a) optical transmission of light of wavelength less than 380 nm.

(b) good adhesion to $TiO_2$.

(c) low solubility in water.

(d) rapid settling in water.

In particular titanium dioxide can be attached to borosilicate glass tubing, glass mesh, glass beads, sand, diatomaceous earth, teflon, and silica gel by the process of the invention and still retain its ability to photo-oxidize organic compounds in water (see Australian Application No. 76028/87 the contents of which are incorporated herein). Furthermore, titanium dioxide has been found to be retained by the supporting material after repeated washing with water.

Some examples of the organic compounds which can be detected using the method of the invention are benzene, phenol, monochlorobenzene, nitrobenzene, aniline, benzoic acid, catechol, resorcinol, hydroquinone, 1,2 dichlorobenzene, 2 bromophenol, 3 iodophenol, thiocresol, sulfosalicylic acid, phosphoserine, 2 chlorophenol, 3 chlorophenol, 4 chlorophenol, 2,4 dichlorophenol, 2,4,6 trichlorophenol, methyl viologen, 2 naphthol, chloroform, salicylic acid, fluorescein, trichloroethylene, ethylene diamine, dichloroethane and formalin.

Aqueous solutions containing these compounds on photocatalytic oxidation produce ionic species such as $HCO_3^-$, $CO_3^{2-}$, $Cl^-$, $Br^-$, $I^-$, $NO_3^-$, $PO_4^{3-}$, $SO_4^{2-}$ and consequently there is a concomitant significant increase in the conductivity of such solutions. It is possible to use the method of the invention to determine the increase in conductivity as a sensitive detector of these compounds and obtain a measurement of the concentration which is not easily obtained by other means. Alcohols, for example, have poor optical absorption characteristics in the ultraviolet region of the spectrum but can readily be detected by an increase in conductivity after photocatalytic oxidation. It is also possible to combine photocatalytic oxidation with conductivity detection in HPLC methods to detect other compounds for which sensitive methods of detection are not readily available. An example of one application of photocatalytic oxidation over thin films of titanium dioxide to chemical analysis is in the detection of formalin.

Preferably a HPLC detector is used to detect the by-product(s). a further preferred form the semiconductor is incorporated into silica gel. It is especially preferred that when semiconductor photocatalytic metal oxides are incorporated into silica gel that the process of incorporation is in accordance with the silica gel incorporation process disclosed in Australian Provisional Specification No PH7074.

In yet a further preferred form the photoreactor is a container or tube and at least a portion of the internal walls of the container or tube are coated with the semiconductor. If the photoreactor is constructed from any of the above substrates it is preferred that the process of coating is one of the coating processes disclosed in Australian Provisional Specification No PH7074. Where the photoreactor is constructed from material that is transparent to light of energy greater than the band gap of the semiconductor it is preferred that the illumination means is disposed external of the reactor so as to illuminate the semiconductor through the photoreactor. For example, where $TiO_2$ is used as the semiconductor the photoreactor can be made of borosilicate glass or quartz since both materials transmit light greater than the band gap of $TiO_2$.

Where the photoreactor is constructed of transparent materials but the internal walls of the photoreactor is coated with a semiconductor the thickness of which is of such magnitude that it significantly attenuates illumination from illumination means disposed external of the photoreactor or the photoreactor is constructed from opaque or substantially opaque material the illumination means can be disposed within the photoreactor.

The illumination means is selected so as to provide light having energy greater than the bandgap of the particular semiconductor chosen. For example, when $TiO_2$ is used the illumination means can be a mercury lamp, a xenon lamp, sunlight, or a near ultraviolet fluorescent tube.

Total inorganic carbonate can be determined by standard procedures. For example, total inorganic carbonate can be determined by acidification of the aqueous solution with no light and measuring the formed carbon dioxide.

The methods of the first and second embodiments and the systems of the third and fourth embodiments have advantages over conventional photooxidation methods and systems since if, for example, a $TiO_2$ photocatalyst is used, the illumination means is more readily available and the $TiO_2$ photocatalyst is chemically stable and may be reused. Since borosilicate glass is transparent to near U.V. light it may be used for construction of the photoreactor thus dispensing with the need for using expensive quartz photoreactors. Solutes transparent to UV light are not readily photooxidized but may be photocatalytically oxidized because the semiconductor is photoactivated although the solute may not be. More uniform oxidation rates for different solutes occur with photocatalytic oxidation. Thus total oxidation and reliable results are more regularly received.

BRIEF DESCRIPTION OF THE DRAWINGS

Systems and methods for qualitatively and quantitatively determining organic matter in an aqueous solution including an oxidizing agent are now described by way of example with reference to the following FIGS. in which.

MODES FOR CARRYING OUT THE INVENTION

Figure 1:
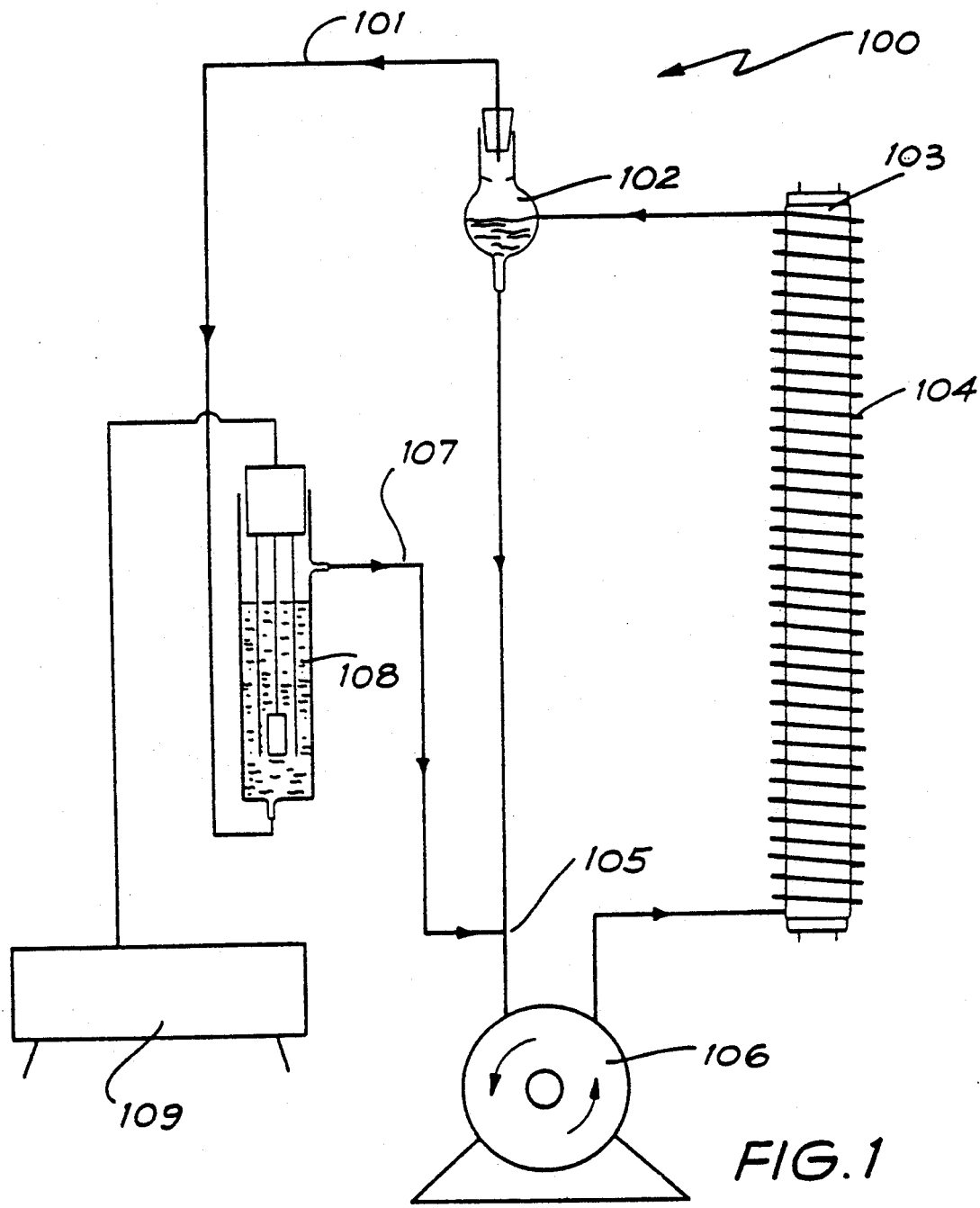
FIG. 1 is a schematic drawing of a system for determining total carbon and total organic carbon in an aqueous solution.

Referring to FIG. 1, a system 100 for determining total carbon and total organic carbon in an aqueous solution includes a spiral borosilicate glass photoreactor 104 through which the aqueous solution is circulated by peristaltic pump 106 via loading port 102 and Tee junction 105. Photoreactor 104 is disposed about 20-12 W U.V. fluorescent tube 103. Conductivity cell 108 is linked with loading port 102 via tube 101 and with Tee junction 105 via tube 107. Cell 108 has associated conductivity meter 109 to measure any conductivity change in cell 108. A thin film of titanium dioxide photocatalyst is coated on the inner surface of photoreactor 104. The thin film coating can be formed according to the coating process disclosed in Australian Provisional Specification No PH7404 or any other suitable coating procedure. Alternatively a small quantity of powdered TiO$_2$ photocatalyst can be added to an aqueous solution recirculated through an uncoated photoreactor 104.

In use an aqueous solution is added to loading port 102 and is pumped around loop 102-105-106-104 by pump 106. Air in tube 107 mixes with the aqueous solution at Tee junction 105 and is pumped through photoreactor 104 in serried ranks of bubbles. The aqueous solution is acidified to liberate carbon dioxide from inorganic carbonates therein. Tube 103 is switched on to illuminate the TiO$_2$ coating causing photocatalytic oxidation to CO$_2$ in photoreactor 104. Bubbles separate from the aqueous solution at loading port 102 and are drawn through conductivity cell 108 via tube 101, whilst the aqueous solution is recirculated via Tee junction 105 where it contacts air again. Recirculation of the aqueous solution is continued until an equilibrium reading is obtained on meter 109. The carbon dioxide formed by acidification of the inorganic carbonates and in photoreactor 104 by photocatalytic oxidation of organic carbon compounds in the acidified aqueous solution equilibrates with the circulating bubbles of air therein. Thus changes in conductance measured in cell 108 are proportional to total carbon dioxide formed which in turn is directly related to total carbon in the aqueous solution. Alternatively, inorganic carbonate can be separately determined from the carbon dioxide formed by acidification of the aqueous solution in the apparatus with no light. The acidified solution can then be optionally purged and total organic carbon determined from the carbon dioxide formed with light on. Total carbon can be calculated from the sum of total organic and inorganic carbon.

The apparatus can be calibrated by injecting measured volumes of carbon dioxide into the apparatus or by adding known volumes of a solution of a primary standard organic compound such as potassium hydrogen phthalate. In the present experiments both techniques were used. The specific conductance of cell 108 is related to the carbon dioxide present by a log/log relationship (FIG. 2), approximately linear at higher carbon dioxide concentrations.

Figure 2:
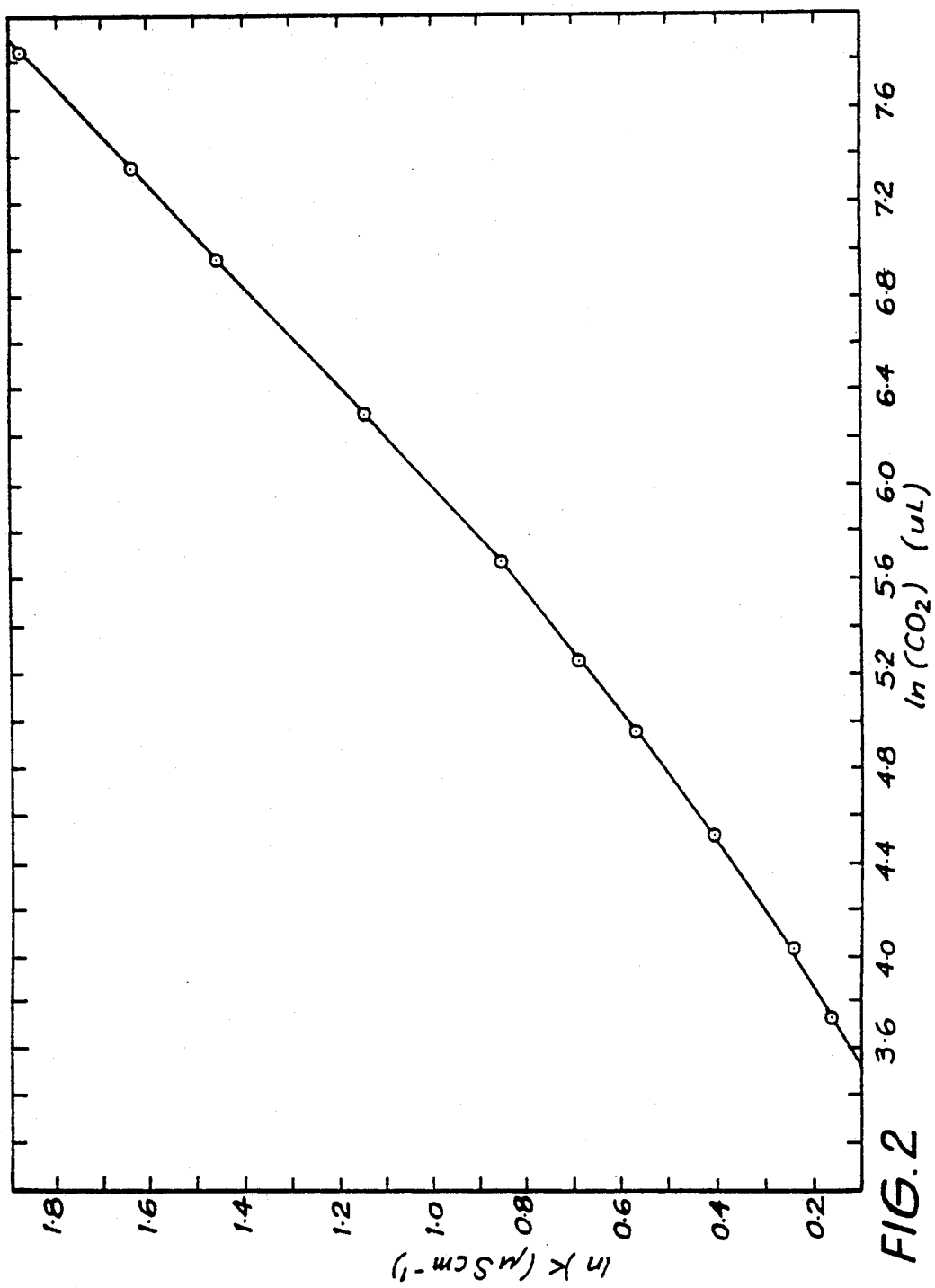
FIG. 2 depicts a calibration curve for response of conductivity cell to total carbon dioxide, 40 mL water in reactor, 40 mL water in cell, both initially aerated, water in reactor acidified to pH 3.0 with perchloric acid.
Figure 3:
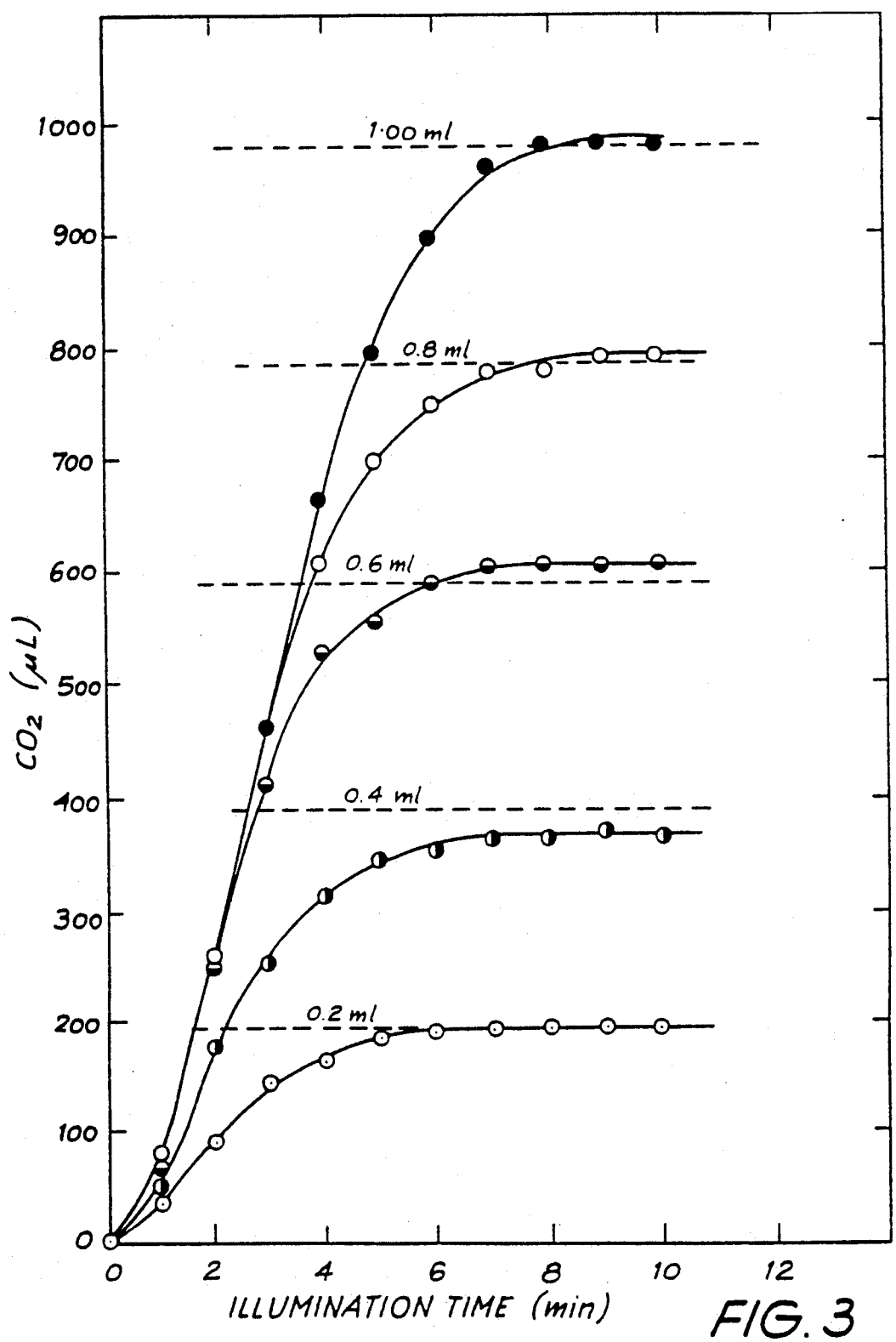
FIG. 3 shows curves of carbon dioxide yield from various volumes of 0.005M potassium hydrogen phthalate solution versus time after addition. Total volume of solution in reactor 40 mL inclusing 0.80 mL 0.02M $HClO_4$. Pump speed 200 mL $min^{-1}$.

Using the calibration curve. FIG. 2, the carbon dioxide formed in system 100 upon addition of various amounts of an 0.005M potassium hydrogen phthalate solution was measured and compared with the calculated theoretical amount of CO$_2$ for 100% conversion. The yield of CO$_2$ as a function of time after addition to the apparatus is shown in FIG. 3 together with the 100% values (dashed lines).

Figure 4:
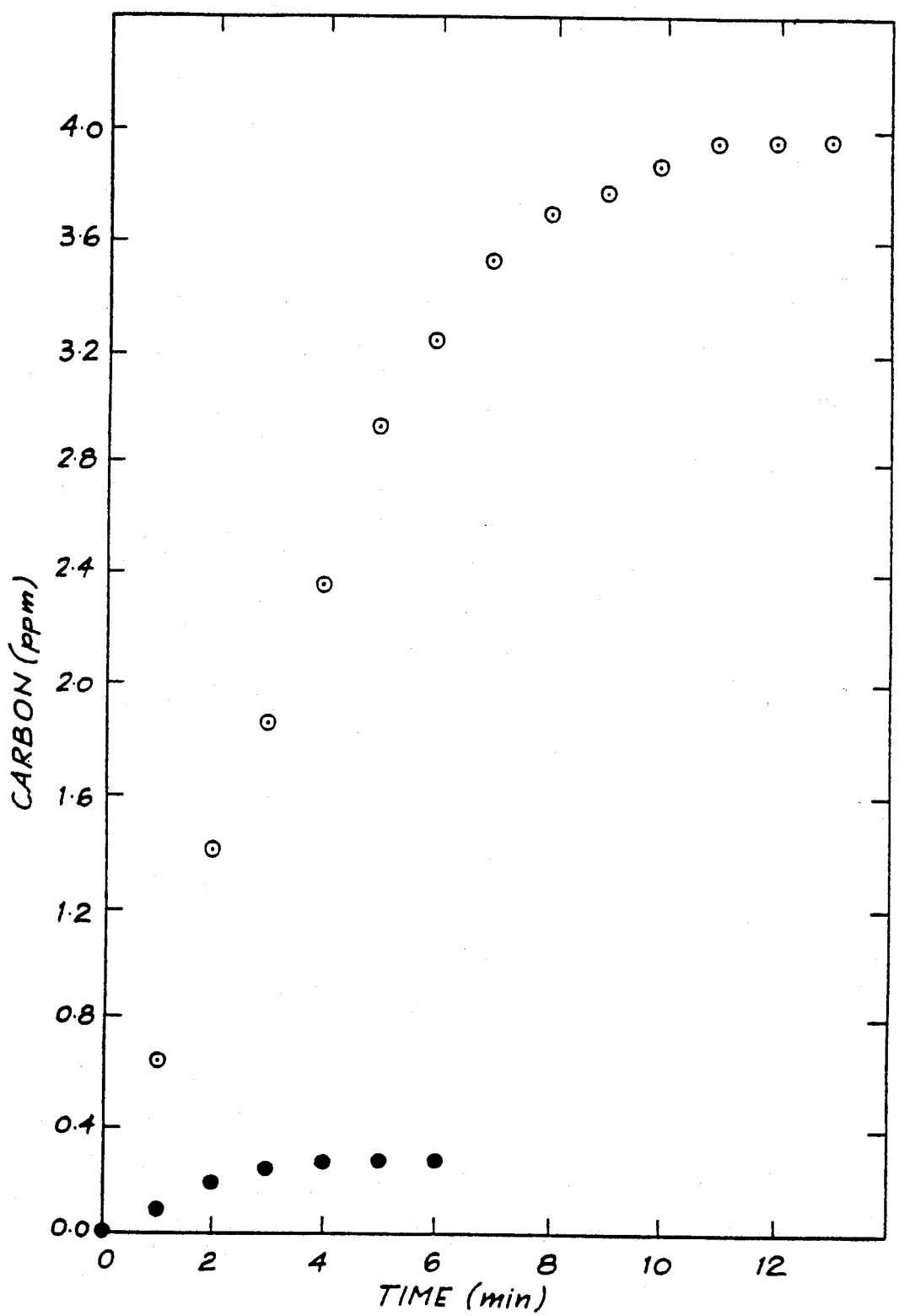
FIG. 4 depicts carbon dioxide yield expressed as ppm C for Sydney mainswater versus time after addition of 40 mL +0.8 mL 0.02M $HClO_4$. Pump speed 200 mL $min^{-1}$.
● no light
⊙ light on FIG. 5 depicts TOC ppm from 2.0 mL sample of $10^{-3}$M nitrobenzene added to 38 mL water+0.80 mL 0.02 $MHClO_4$. Solar illumination using 0.25 $m^2$ parabolic trough. Pump speed 200 mL $min^{-1}$.

The inorganic carbon and total carbon from a 40 mL sample of Sydney mainswater was determined in system 100 and the results are shown in FIG. 4. The TOC is below the limit of accurate detection of many combustion TOC analyzers.

Figure 5:
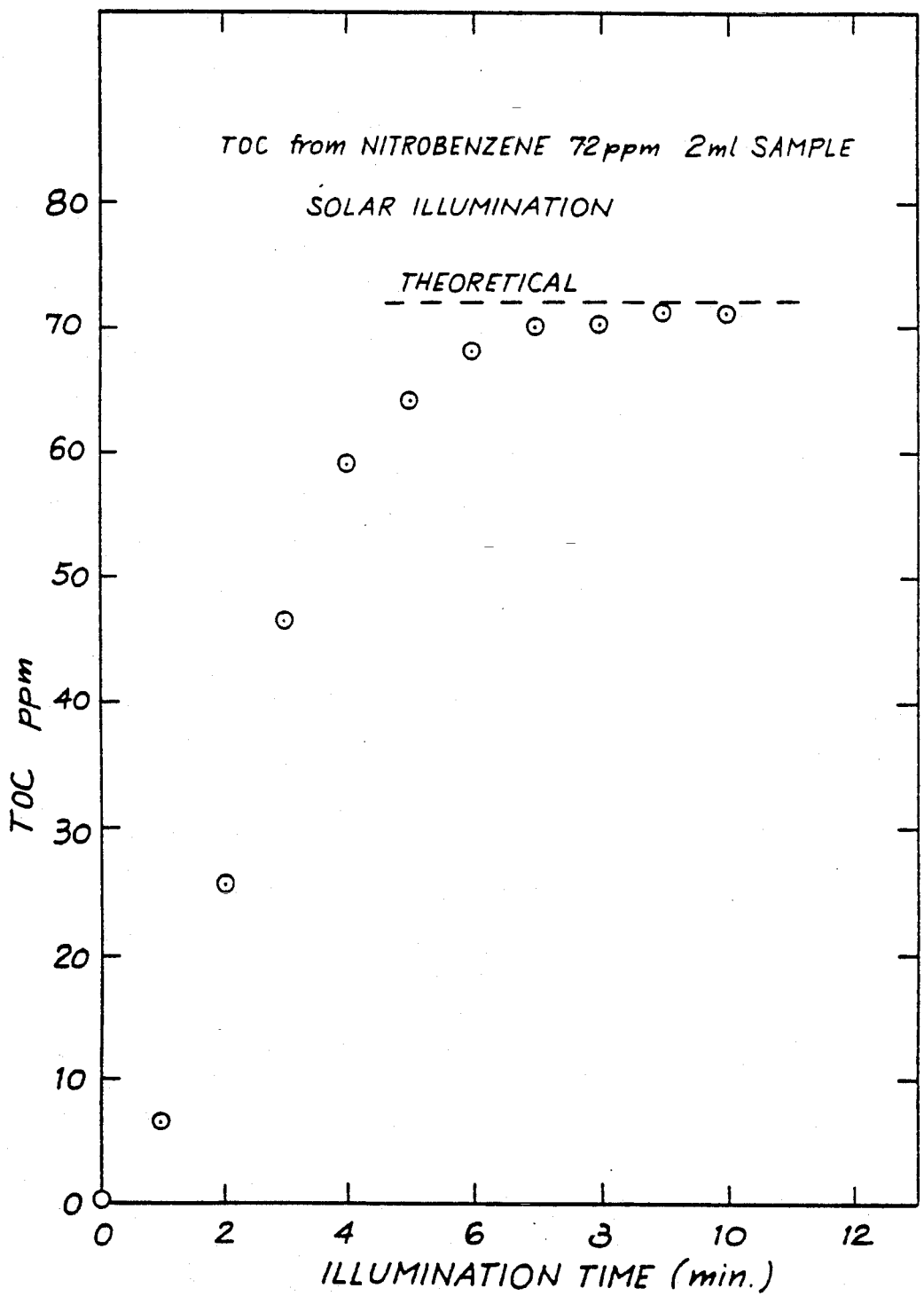

In other experiments U.V. fluorescent tube 103 was removed and photoreactor 104 located at the focus of an 0.25 m$^2$ parabolic trough. The results shown in FIG. 5 were obtained using direct sunlight. The solution to be analyzed for TOC contained 72 ppm carbon in the form of nitrobenzene.

Results obtained using the U.V. fluorescent tube as the light source (maximum emission at 365 nm) and standard solutions of different substances are given in Table 1.

TABLE 1

| Compound | Carbon in Standard Solution ppm | | |
|---|---|---|---|
| | Calculated | Found | % Recovery |
| Potassium biphthalate | 480 | 484 | 100.8 |
| Ethanol | 24.0 | 24.1 | 100.4 |
| 7-Hydroxylcoumarin | 108 | 106 | 98.4 |
| Nitrobenzene | 72.0 | 71.0 | 98.6 |
| Acetic Acid | 237 | 232 | 97.9 |
| Toluene | 83.9 | 79.5 | 94.7 |
| Salicylic acid | 83.9 | 85.6 | 102.0 |
| Benzoic acid | 83.9 | 85.1 | 101.5 |
| Sucrose | 72.1 | 78.5 | 108.8 |
| Chloroform | 120.2 | 122.7 | 102.0 |

Figure 6:
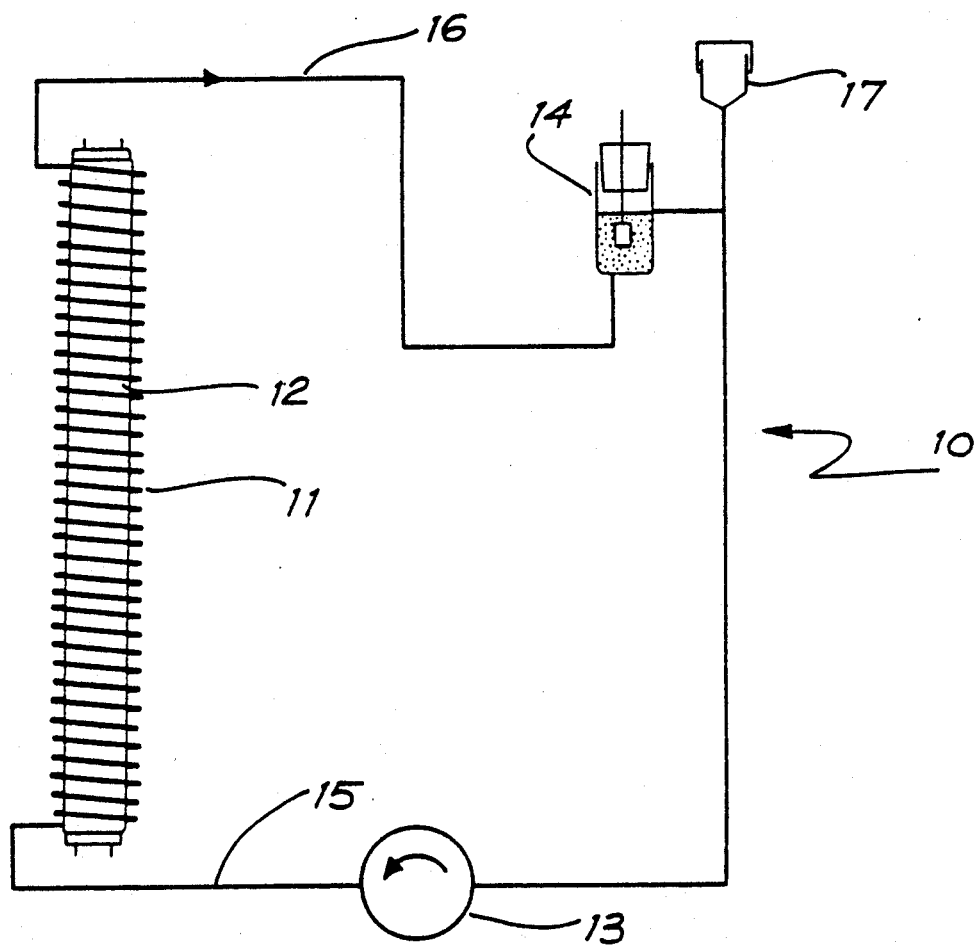
FIG. 6 is a schematic drawing of a system for detecting the presence of or determining the concentration of an organic matter in an aqueous solution including an oxidizing agent.

Referring to FIG. 6, a system 10 for detecting the presence of or determining the concentration of an organic compound in water or an aqueous composition including an oxidising agent includes a photochemical reactor 11 spirally disposed about a UV fluorescent tube 12. A thin film of titanium dioxide is attached to the inner surface of tube 11. The water or aqueous composition is poured into reservoir 17 and recirculated through tube 11 and connecting tubes 15 and 16 by pump 13 via conductivity cell 14.

The presence of an organic compound in water or an aqueous composition is detected using system 10 by filling reservoir 17 with the water or aqueous composition. The water or aqueous composition which has been exposed to ambient oxygen, is recirculated through tube 15, photoreactor 11 and tube 16 via conductivity cell 14 by pump 13 and the initial conductivity of the liquid is measured using cell 14 with tube 12 inactivated. Tube 12 is then activated so that it illuminates the coating of TiO$_2$ in photoreactor 11 so as to photocatalytically-oxidize any organic compound present in the recirculating liquid. After the recirculating liquid has been illuminated for a selected time (typically 5 to 30 minutes, more typically 8 to 12 minutes) so that any organic compound present in the liquid is substantially oxidized the final conductivity of the liquid is measured using cell 14. The initial and final conductivities are compared with each other. When there is no organic compound present in the liquid the initial and final conductivities are the same. When an organic compound is present in the liquid the final conductivity is greater than the initial conductivity due to the presence of oxidized by-products of the organic compound in the water or aqueous composition.

The concentration of an organic compound in water or an aqueous composition is determined using system 10 by filling reservoir 17 with the water or aqueous composition. The initial and final conductivities of the water or aqueous composition are determined in an analogous manner to the method described above for determining the presence of an organic compound in water or an aqueous composition. The initial and final conductivities are then compared with each other and the concentration of the organic compound is ascertained from the magnitude of the difference between the initial and final conductivities.

EXAMPLE

High purity water (40 mL) was circulated through the spiral photoreactor coated with a thin film of TiO$_2$ as used in the total organic carbon analyzer in series with a conductivity cell as shown in FIG. 1. On switching on the 20 W blacklight fluorescent lamp inserted down the centre of the spiral the conductivity in the cell increased marginally with illumination time as shown by the results in Table 1 column 2. When 0.10 mL of a 1% formalin solution (giving a 15 ppm solution of HCHO) was added, a significant increase in conductivity was obtained shown by the results in column 3 of Table 1.

TABLE 1

Increase in Conductivity of Solution on Illumination Apparatus of FIG. 1

| Illumination Time (min) | Conductivity No HCHO ($\mu S\ cm^{-1}$) | 15 ppm HCHO ($\mu S\ cm^{-1}$) |
|---|---|---|
| 0 | 1.22 | 1.21 |
| 1 | 1.23 | 1.40 |
| 2 | 1.23 | 1.70 |
| 3 | 1.24 | 2.01 |
| 4 | 1.24 | 2.23 |
| 5 | 1.25 | 2.40 |
| 6 | 1.25 | 2.50 |
| 7 | 1.26 | 2.56 |
| 8 | 1.27 | 2.60 |
| 9 | 1.27 | 2.62 |
| 10 | 1.28 | 2.62 |

System 10 can be calibrated using known amounts of formaldehyde to enable the quantitative estimation of formaldehyde in the solution from the increase in conductivity. Similar experiments can be run with other organic compounds.

INDUSTRIAL APPLICABILITY

The methods and systems of the invention are particularly suitable for detection or measurement of low total carbon concentrations (less than 1 ppm) in an aqueous solution.

I claim:

1. A method for determining organic matter in an aqueous solution including an oxidizing agent, said organic matter being photooxidizable with the aid of a photocatalyst to form at least one photocatalytic by-product, said method comprising:
   a) passing the solution through a vessel which contains the photocatalyst coated on a surface of the vessel while
      i) illuminating the photocatalyst with ultraviolet light from an illumination source disposed externally to the vessel such that the photocatalyst coating the surface of the vessel is disposed between the source of ultraviolet light and the solution; and
      ii) maintaining the photocatalyst in sufficiently close contact with the illumination source and maintaining the solution in contact with a sufficiently large area of the photocatalyst over a sufficient length of vessel such that the solution is substantially wholly oxidized to form said at least one by-product by means consisting essentially of a phototcatalytic oxidation, and
   b) detecting said at least one photocatalytic by-product.

2. A method as defined in claim 1 wherein said at least one photocatalytic by-product comprises inorganic carbonates and said method further comprises acidifying said aqueous solution after step (a) thereby converting said inorganic carbonates to carbon dioxide.

3. The method of claim 1 in which the oxidizing agent is oxygen.

4. A method as defined in claim 1 wherein said at least one photocatalytic by-product by measuring the change in an electrical characteristic of said solution caused by said photocatalytic oxidation.

5. A method as defined in claim 4 wherein the electrical characteristic is conductivity.

6. A method as defined in claim 1 wherein said solution is agitated during said illuminating.

7. A method as defined in claim 6 wherein said agitating comprises pumping air or oxygen through said solution and said aqueous solution is an acidified aqueous solution whereby said at least one photocatalytic by-product comprises carbon dioxide.

8. A method for quantitatively determining organic matter in an aqueous solution comprising the method as defined in claim 1 and further comprising:
   (d) measuring a parameter of said at least one photocatalytic by product related to the concentration or amount thereof; and
   (e) determining the concentration of the organic matter in said solution from the parameter.

9. A method as defined in claim 8 wherein said at least one photocatalytic by-product is detected by measuring a change in an electrical characteristic of said solution caused by said photocatalytic oxidation, further comprising determining the amount of said at least one photocatalytic by-product from the magnitude of said change and determining the concentration of said organic matter from said amount.

10. A method as defined in claim 9 wherein the electrical characteristic is conductivity.

11. A method as defined in claim 1 further comprising acidifying said aqueous solution and wherein said at least one photocatalytic by-product comprises carbon dioxide.

12. A method as defined in claim 11 further comprising purging said carbon dioxide from said aqueous solution with a gas other than carbon dioxide and detecting said purged carbon dioxide.

13. A method as defined in claim 12 further comprising determining the amount of said purged carbon dioxide and determining total carbon concentration in said solution from the amount of said purged carbon dioxide.

14. A method as defined in claim 13 the amount of said purged carbon dioxide by dissolving said purged carbon dioxide in water and measuring the change in conductivity of said water caused by said dissolving.

15. A system for qualitatively determining organic matter in an aqueous solution including an oxidizing agent, said system comprising
   (i) a semiconductor,
   (ii) a photocatalytic reactor in which to photocatalytically-oxidize the organic matter in the solution, said reactor comprising vessel means for maintaining said solution in contact with said semiconductor, said vessel means having a surface or surfaces coated with said semiconductor and forming a path for said solution to pass,
   (iii) an illumination source of ultraviolet light disposed to illuminate the semiconductor with ultraviolet light whereby upon illumination of the semiconductor the organic matter in the solution is oxidized to form at least one photocatalytic by-product, said illumination source being disposed externally to said vessel means such that the semiconductor coating said vessel means is disposed between the UV light and the solution, said vessel means maintaining the semiconductor in sufficiently close contact with said illumination source and maintaining the solution in contact with a sufficiently large area of the semiconductor over a sufficiently long path such that the organic matter in the solution is substantially wholly oxidized to form said at least one by-product by means consisting essentially of a photocatalytic oxidation and (iv) means for detecting said at least one photocatalytic by-product, operatively associated with or operatively coupled to the reactor.

16. A system as defined in claim 15 wherein said means for detecting is a conductivity cell which is operatively associated with or operatively coupled to the reactor.

17. A system as claimed in claim 15, wherein said vessel means comprises a tube of borosilicate glass.

18. A system for quantitatively determining organic matter in an aqueous solution comprising the system as defined in claim 15 and further comprising:

(iv) means for measuring a parameter of said at least one photocatalytic by-product related to the concentration or amount thereof, operatively associated with or operatively coupled to said means for detecting said at least one photocatalytic by-product.

19. A system as defined in claim 18 further comprising:

(v) calculating means operatively associated with or operatively coupled to said means for measuring a parameter, for calculating the concentration of the organic matter in said solution from the measured parameter of said at least one photocatalytic by-product.

20. A system as defined in claim 15 wherein said at least one by-product comprises carbon dioxide, the system further comprising means for purging said carbon dioxide from said aqueous solution with a gas other than carbon dioxide, said means for detecting being constructed so as to detect said purged carbon dioxide and said means for purging being operatively associated with or operatively coupled to the reactor.

21. A system as defined in claim 20 wherein said means for detecting is a conductivity cell.

22. A system as defined in claim 15 further comprising means for agitating said solution, operatively associated with or operatively coupled to the reactor.

23. A system as defined in claim 22 wherein said means for agitating is a pump.

* * * * *